United States Patent [19]
Hirsch

[11] 4,086,278
[45] Apr. 25, 1978

[54] 1-ALKENYL THIOETHERS

[75] Inventor: Allen Frederick Hirsch, Somerville, N.J.

[73] Assignee: Ortho Pharmaceutical Corporation, Raritan, N.J.

[21] Appl. No.: 666,818

[22] Filed: Mar. 15, 1976

[51] Int. Cl.$^2$ .................... A61K 31/10; C07C 149/18; C07C 149/20
[52] U.S. Cl. .......................... 260/609 R; 260/340.9 R; 260/399; 260/402.5; 260/403; 260/944; 260/945; 560/20; 560/100; 560/111; 560/113; 560/201; 424/337
[58] Field of Search ................................ 260/609 R

[56] References Cited

U.S. PATENT DOCUMENTS

| | | | |
|---|---|---|---|
| 3,062,892 | 11/1962 | Schneider | 260/609 R |
| 3,118,002 | 1/1964 | Benzing et al. | 260/609 R |
| 3,350,460 | 10/1967 | Lamberti | 260/609 R |
| 3,544,636 | 12/1970 | Distler et al. | 260/609 R |
| 3,729,518 | 4/1973 | Mulhein et al. | 260/609 A |

OTHER PUBLICATIONS

Chem. Abst., vol. 24, pp. 3750, 3751, (1930).

Primary Examiner—Joseph Paul Brust
Assistant Examiner—Molly C. Eakin
Attorney, Agent, or Firm—Benjamin F. Lambert

[57] ABSTRACT

1-Alkenyl thioethers of glycols are described. The alkenyl thioethers possess central nervous system activity and are useful as tranquilizers.

4 Claims, No Drawings

1-ALKENYL THIOETHERS

The present invention relates to 1-alkenyl thioethers. The novel compounds are thioethers of glycols such as ethylene glycol or glycerol and the corresponding ester, ether, acetal, ketal or halogen derivatives thereof and can be represented by the following formulae:

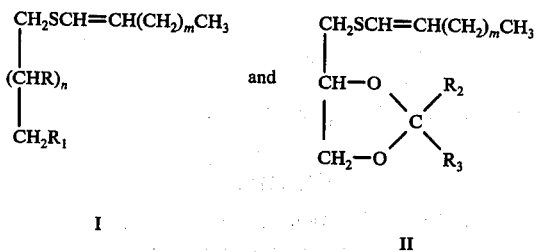

I                        II wherein R is hydroxy, alkoxy having 1–18 carbon atoms, halo, thiol, alkylthio wherein the alkyl group has 1–18 carbon atoms, and —OCOR' wherein R' is aryl or substituted aryl such as phenyl, α-naphthyl, β-naphthyl, chlorophenyl, nitrophenyl and alkylphenyl wherein the alkyl group has 1–3 carbon atoms, and alkyl wherein the alkyl group has 1–18 carbon atoms; $R_1$ is hydroxy, alkoxy having 1–18 carbon atoms, halo, thiol, alkylthio, —OCOR' wherein R' is aryl or substituted aryl such as phenyl, α-naphthyl, β-naphthyl, chlorophenyl, nitrophenyl and alkylphenyl wherein the alkyl group has 1–3 carbon atoms, and alkyl wherein the alkyl group has 1–18 carbon atoms, and —OP (OB) (O) (OH) wherein B is an aminoalkyl, alkylaminoalkyl or a dialkylaminoalkyl group, wherein the alkyl group has 1–3 carbon atoms such as, for example, aminoethyl, methylaminoethyl, dimethylaminomethyl and dimethylaminopropyl; m is an integer from 0–17; n is an integer from 0–1; $R_2$ is hydrogen, lower alkyl such as methyl, ethyl, butyl and the like or aryl or substituted aryl such as phenyl, α-naphthyl, β-naphthyl, chlorophenyl, nitrophenyl and alkylphenyl wherein the alkyl group has 1–3 carbon atoms; and $R_3$ is lower alkyl such as methyl, ethyl, butyl, pentyl and the like, aryl or substituted aryl; and the pharmaceutically acceptable quarternary salts thereof where $R_1$ is —OP (OB) (O) (OH).

The novel compounds of the present invention are capable of modifying the central nervous system, particularly as depressants, and are therefore useful as tranquilizers.

Those compounds wherein R is hydroxy, alkoxy, thiol or alkylthiol, $R_1$ is hydroxy, halogen or thiol, $R_2$ is hydrogen, lower alkyl, aryl or substituted aryl and $R_3$ is lower alkyl, aryl or substituted aryl are prepared by first reacting the appropriate 1-lower alkylthio-1-alkene, wherein the alkyl group has 1–4 carbon atoms, such as 1-ethylthio-1-octadecene, 1-propylthio-1-heptene, and the like with an alkali metal in ammonia followed by reaction with an appropriately substituted halo compound such as for example 1-bromo-2,3-propanediol, 1-bromo-2,3-propanedithiol, 1,2-bis (pentylthio)-3-bromopropane, 4-bromomethyl-2-pentyl-1,3-dioxolane, 1,2-bis(pentyloxy)-3-bromopropane, ethylenebromohydrin, 1-bromo-3-chloro-2-propanol, 4-bromomethyl-2-phenyl-1,3-dioxolane and the like. The reaction with the alkali metal is generally carried out in dry liquid ammonia. The reaction with the 1-alkylthio-1-alkene is generally carried out by adding a solution of the compound to the liquid ammonia mixture. Solvents which can be employed include ether, tetrahydrofuran, dioxane and the like.

Those compounds wherein R and $R_1$ are —OCOR' are prepared by reacting the appropriate 1-alkenylthioglycol with an acid halide or acid anhydride such as acetyl chloride, hexanoyl chloride, butyryl chloride, acetic anhydride and the like in the presence of a suitable base such as pyridine, triethylamine or N-methylpiperidine.

Those compounds wherein $R_1$ is —OP (OB) (O) (OH) are prepared by a series of reactions using an appropriately substituted 1-alkenylthio glycol as the starting material. The 1-alkenylthio glycol is first reacted with a sulfonyl halide such as p-toluenesulfonyl chloride, for example in a suitable solvent. Solvents which may be employed include chloroform, methylene chloride, ether and benzene. The reaction is generally carried out in the presence of an amine such as pyridine, triethylamine, N-methylpiperidine and the like, for example at a temperature between 0° C and room temperature. In those cases where n=1, an acid halide is then added to the solution of the reaction mixture. Acid halides which may be employed include acetyl chloride, propionyl chloride, benzoyl chloride and the like. It is preferred to carry out the reaction in the presence of an amine such as pyridine, for example. The resulting sulfonate is then reacted with an alkali metal iodide in a solvent, preferably in the presence of an amine such as pyridine for example. Solvents which may be employed include acetone and methylethyl ketone. The product of this reaction is then treated with silver dibenzyl phosphate in a suitable solvent. The reaction is preferably carried out at the reflux temperature of the solvent. Solvents such as benzene, xylene, toluene and the like may be employed for the reaction. The reaction product is then treated with an alkali metal iodide such as sodium iodide, for example, in the presence of an amine followed by treatment with silver nitrate. Solvents which may be employed for this reaction include acetone, methylethyl ketone, acetone-water and the like. The resulting silver salt is then reacted with an amino halide such as 2-chloro-N,N-(dimethyl)ethylamine. The resulting product is treated with an alkali metal iodide such as sodium iodide, for example, and the metal salt is then treated with a cation exchange resin to obtain the phosphoryl ester compound.

The compounds used as the starting materials in the preparation of the novel 1-alkenyl thioethers of glycols, i.e. the 1-loweralkylthio-1-alkenes, are prepared by reacting a 1,1-di-(alkylthio)-alkane such as, for example, 1,1-di-(ethylthio)-octadecane, with potassium bisulfate at elevated temperatures. Those compounds wherein m is 0–5 are prepared by substituting phosphoric acid for potassium bisulfate. The 1-loweralkylthio-1-alkene is obtained from the reaction mixture by techniques known to those skilled in the art.

The following examples describe the invention in greater particularity and are intended to be a way of illustrating but not limiting the invention.

EXAMPLE 1

3-(1-Heptenylthio)-1,2-propanediol

Lithium (1.61 g., 0.234 eq.) cut into small pieces is added to 150 ml. of dry liquid ammonia with stirring. After 5 minutes, 100 ml. of dry ether is added followed by the dropwise addition of 1-ethylthio-1-heptene (18.6 g., 0.117 moles). At the end of the addition, the blue color of the solution disappears and the reaction mixture is a white milky suspension. Ammonium chloride (6.26 g., 0.117 moles) is added cautiously followed by 1-bromo-2,3-propanediol (19.9 g., 0.128 moles). After stirring for 30 minutes, the ammonia is allowed to evaporate and water and ether are added to the residue. The aqueous layer is extracted once with ether and the ether extracts are combined and dried over MgSO$_4$. The residue obtained after concentration of the ether is distilled (bp 129°–133° C, 0.15 mm.) to afford 6 g. of a yellow liquid. The liquid is further purified by column chromatography on SilicAR, CC-7, eluting with acetone:-chloroform (1:5) to afford 3-(1-heptenylthio)-1,2-propanediol as a colorless liquid (5.7 g., 23.9%); $n_D^{24.1}$ 1.5091.

When in the above procedure 1-ethylthio-1-octadecene and 1-ethylthio-1-dodecene are employed in place of 1-ethylthio-1-heptene, 3-(1-octadecenylthio)-1,2-propanediol and 3-(1-dodecenylthio)-1,2-propanediol are obtained.

EXAMPLE 2

3-(1-Heptenylthio)-1,2-propanedithiol

When 1-bromo-2,3-propanedithiol (24.0 g., 0.128 mol.) is employed as the halogen in the procedure of Example 1, 3-(1-heptenylthio)-1,2-propanedithiol is obtained.

EXAMPLE 3

2-(1-Heptenylthio)-1-ethanol

When ethylenebromohydrin (16.3 g., 0.128 moles) is employed as the halogen in the procedure of Example 1, 2-(1-heptenylthio)-1-ethanol is obtained.

EXAMPLE 4

4-(1-Heptenylthiomethyl)-2-pentyl-1,3-dioxolane

When 4-bromomethyl-2-pentyl-1,3-dioxolane (30.8 g., 0.128 moles) is employed as the halogen in the procedure of Example 1, 4-(1-heptenyl-thiomethyl)-2-pentyl-1,3-dioxolane is obtained.

When in the above procedure 4-bromomethyl-2-phenyl-1,3-dioxolane, 4-bromomethyl-2-phenyl-2-methyl-1,3-dioxolane and 4-bromomethyl-2-methyl-2-propyl-1,3-dioxolane are employed in place of 4-bromomethyl-2-pentyl-1,3-dioxolane, 4-(1-heptenylthiomethyl)-2-phenyl-1,3-dioxolane, 4-(1-heptenylthiomethyl)-2-phenyl-2-methyl-1,3-dioxolane and 4-(1-heptenylthiomethyl)-2-methyl-2-propyl-1,3-dioxolane are obtained.

EXAMPLE 5

3-(1-Heptenylthio)-1,2-bis-(pentyloxy)-propane

When 1,2-bis-(pentyloxy)-3-bromopropane (37.5 g., 0.128 moles) is employed as the halogen in the procedure of Example 1, 3-(1-heptenylthio)-1,2-bis-(pentyloxy)-propane is obtained.

When in the above procedure 1,2-bis(octadecyloxy)3-bromopropane and 1,2-bis-(dodecyloxy)-3-bromopropane are employed in place of 1,2-bis-(pentyloxy)-3-bromopropane, 3-(1-heptenylthio)-1,2-bis-(octadecyloxy)-propane and 3-(1-heptenylthio)-1,2-bis-(dodecyloxy)-propane are obtained.

EXAMPLE 6

3-(1-Heptenylthio)-1-chloro-2-propanol

When 1-bromo-3-chloro-2-propanol (22.1 g., 0.128 moles) is employed as the halogen in the procedure of Example 1, 3-(1-heptenylthio)-1-chloro-2-propanol is obtained.

EXAMPLE 7

3-(1-Heptenylthio)-1,2-dichloropropane

When 1-bromo-2,3-dichloropropane (24.4 g., 0.128 moles) is employed as the halogen in the procedure of Example 1, 3-(1-heptenylthio)-1,2-dichloropropane is obtained.

EXAMPLE 8

3-(1-Heptenylthio)-1,2-bis hexanoyloxypropane

Hexanoyl chloride (13.5 g., 0.1 mole) in dry carbon tetrachloride (25 ml.) is added slowly to a solution of 3-(1-heptenylthio)-1,2-propanediol (1.04 g., 0.005 moles) and pyridine (4 ml.) in carbon tetrachloride (25 ml.). The mixture is stirred at 0° for 4 hrs. and left overnight at room temperature. Water (10 ml.) is added and the mixture is stirred for 30 minutes, washed with saturated sodium bicarbonate, water, dried over MgSO$_4$ and concentrated to afford 3-(1-heptenylthio)-1,2-bis-hexanoyloxypropane.

When in the above procedure benzoyl chloride, propionyl chloride and octadecanoyl chloride are employed in place of hexanoyl chloride, 3-(1-heptenylthio)-1,2-bis benzoyloxypropane, 3-(1-heptenylthio)-1,2-bis propionyloxypropane and 3-(1-heptenylthio)-1,2-bis octadecanoyloxypropane are obtained.

When in the above procedure p-chlorobenzoyl chloride, p-nitrobenzoyl chloride and p-methylbenzoyl chloride are employed in place of hexanoyl chloride, 3-(1-heptenylthio)-1,2-bis (p-chlorobenzoyloxy)propane, 3-(1-heptenylthio)-1,2-bis (p-nitrobenzoyloxy)-propane and 3-(heptenylthio)-1,2-bis (p-methylbenzoyloxy)propane are obtained.

EXAMPLE 9

3-(1-Heptenylthio)-1,2-bis-(pentylthio)-propane

When 1,2-bis-(pentylthio)-3-bromopropane (41.5 g., 0.128 moles) is employed as the halogen in the procedure of Example 1,3-(1-heptenylthio)-1,2-bis-(pentylthio)-propane is obtained.

EXAMPLE 10

O-[3-(1-Heptenylthio)-2-O-stearoyl-glycero-1-phosphoryl]-2-dimethylaminoethanol

A solution of p-toluenesulfonyl chloride (1.9 g., 0.01 mole) in chloroform (25 ml.) is added with stirring to a solution of 3-(1-heptenylthio)-1,2-propanediol (2.0 g., 0.01 mole) in chloroform (25 ml.) and pyridine (0.79 g., 0.01 mole). The mixture is allowed to stand for 24 hrs. at 0°. The chloroform is washed with water, dried (MgSO$_4$) and concentrated. To the residue dissolved in chloroform is added a solution of stearoyl chloride (3.0 g., 0.01 mole) in pyridine (0.79 g., 0.01 mole) and chloroform (25 ml.) at 0°. The reaction mixture is allowed to stand for 26 hrs. at 18°–20° and is then diluted with ether (30 ml.). The solution is washed with a 5% potassium carbonate solution (2 × 20 ml.), dried (MgSO$_4$) and concentrated. Sodium iodide (3.0 g., 0.02 mole) in acetone (20 ml.) and pyridine (0.79 g., 0.01 mole) is added to the residue. The mixture is refluxed for 6 hours. After dilution with ether (20 ml.) and water (50 ml.), the ether layer is washed with 10% sodium thiosulfate and dried (MgSO$_4$). After removing the solvent, the residue is dissolved in xylene (3 ml.) and pyridine (0.79 g., 0.01 mole) and treated with silver dibenzyl phosphate (3.85 g., 0.01 mole) at reflux temperature in the absence of light for 30 minutes. The mixture is cooled to 18°–20° and the precipitate which forms is removed and washed with ether (10 ml.). The filtrates are combined, dried and concentrated. The product is refluxed with sodium iodide (1.5 g., 0.01 mole), acetone (30 ml.) and pyridine (0.79 g., 0.01 mole) for 3 hours. The mixture is cooled to −5° and the precipitate is filtered, dried and dissolved in acetone (20 ml.) and treated with a solution of silver nitrate (1.7 g., 0.01 mole) in acetone (20 ml.) and water (10 ml.) for 2 hours at 0°. The precipitate is filtered and dried. The residue and 2-chloro-N,N-(dimethyl) ethylamine (1.1 g., 0.01 mole) in benzene is stirred for 2 hours at 80°–85°. The mixture is cooled to 0° and the precipitate is filtered and washed with benzene (5 ml.); the combined filtrates are concentrated, dried and treated with sodium iodide (1.5 g., 0.01 mole) in acetone (30 ml.) and pyridine (0.79 g., 0.01 mole) at reflux for 3 hours. Upon cooling to −5°, the sodium salt is filtered, dissolved in aqueous ethanol, treated with a cation exchange resin (Amberlite IRC-50) to afford O-[3-(1-heptenylthio)-2-O-stearoyl-glycero-1-phosphoryl]-2-dimethylaminoethanol.

When in the above procedure caproyl chloride, valeroyl chloride and butyryl chloride are employed in place of stearoyl chloride, O-[3-(1-heptenylthio)-2-O-caproylglycero-1-phosphoryl]-2-dimethylaminoethanol, O-[3-(1-heptenylthio)-2-O-valeroyl-glycero-1-phosphoryl]-2-dimethylaminoethanol, and O-[3-(1-heptenylthio)-2-O-butyryl-glycero-1-phosphoryl]-2-dimethylaminoethanol are obtained.

When in the above procedure 3-(1-octenylthio)-1,2-propanediol, 3-(1-heptadecenylthio)-1,2-propanediol and 3-(1-tetradecenylthio)-1,2-propanediol are employed in place of 3-(1-heptenylthio)-1,2-propanediol, O-[3-(1-octenylthio)-2-O-stearoyl-glycero-1-phosphoryl]-2-dimethylaminoethanol, O-[3-(1-heptadecenylthio)-2-O-stearoyl-glycero-1-phosphoryl]-2-dimethylaminoethanol and O-[3-(1-tetradecenylthio)-2-O-stearoyl-glycero-1-phosphoryl]-2-dimethylaminoethanol are obtained.

When in the above procedure 2-chloro-N-methylethylamine, N-methylchloromethylamine, 2-chloroethylamine, 2-chloro-N,N-(diethyl)ethylamine and trimethyl-β-bromoethylammonium bromide are employed in place of 2-chloro-N,N-(dimethyl) ethylamine, O-[3-(1-heptenylthio)-2-O-stearoyl-glycero-1-phosphoryl]-2-methylaminoethanol, O-[3-heptenylthio)-2-O-stearoyl-glycero-1-phosphoryl]-methylaminomethanol, O-[3-(1-heptenylthio)-2-O-stearoyl-glycero-1-phosphoryl]-aminoethanol, O-[3-(1-heptenylthio)-2-O-stearoyl-glycero-1-phosphoryl]-2-diethylaminoethanol and O-[3-(1-heptenylthio)-2-O-stearoyl-glycero-1-phosphoryl]-2-trimethylammonioethanol bromide are obtained.

PREPARATION OF 1-ALKYLTHIO-1-ALKENES

A. 1-Ethylthio-1-octadecene

Potassium bisulfate (4 g.) is added to 1,1-di(ethylthio)-octadecane (20 g.) and the resulting mixture is heated under vacuum (200–250 mm.) at 195° C for 6 hrs., cooled to room temperature and dissolved in ether (100 ml.). The ether solution is washed with aqueous sodium bicarbonate and water and then dried over MgSO$_4$. The solvent is removed and the residue is distilled twice to afford 1-ethylthio-1-octadecene (b.p. 181°–183°, 0.8 mm.) as a colorless liquid.

B. 1-Ethylthio-1-heptene

A mixture of 1,1-di(ethylthio)-heptane (54.5 g., 10.25 mole) and 10 drops of 89% phosphoric acid is heated in a Claisen flask at a pressure of 200–250 mm. Care is taken that the vapor temperature does not exceed 165°. The receiver is cooled with water so that ethanethiol does not condense. The distillate is diluted with ether and washed with 2 N sodium hydroxide and water and dried. Distillation (87°–90°/12 mm.) afforded 1-ethylthio-1-heptene (30 g., 78%), $n_D^{20}$ 1.4760.

The compounds of this invention possess central nervous system modifying activity, particularly as depressants and are therefore useful as tranquilizers. The compounds are administered in doses ranging from 10–300 mg./kg. The preferred range, however, is 30–100 mg./kg. The compounds can be administered intraperitoneally, but oral and parenteral administration are also contemplated.

PREPARATION OF SUBSTITUTED HALO COMPOUNDS

A. 1-Bromo-2,3-propanedithiol

Hydrobromic acid (200 ml.) is added to 3-hydroxy-1,2-propanedithiol (100 g.). The mixture is stirred for 48 hours, diluted with water (100 ml.) and extracted with ether (3 × 200 ml.). The extracts are washed with brine, dried, and the ether is removed under reduced pressure to afford 1-bromo-2,3-propanedithiol.

B. 1,2-Bis-(pentylthio)-3-bromopropane

Pentyl bromide (15.1 g., 0.1 mole) is added to a solution of 2,3-dimercaptopropanol (6.2 g., 0.05 mole) and sodium hyroxide (4 g., 0.1 mole) in water (30 ml.) under nitrogen. The mixture is stirred and heated at 100° for 4 hours. After cooling, the mixture is extracted with ether (3 × 50 ml.), dried and concentrated. To the residue dissolved in methylene chloride (50 ml.) and triethylamine (7.5 g.) at 0° to −10° is added methanesulfonyl chloride (6.3 g.). After stirring for 15 minutes, the mixture is extracted with ice water (2 × 10 ml.), cold 10% hydrochloric acid (2 × 5 ml.) and brine (2 × 5 ml.). The methylene chloride is dried (MgSO$_4$) and concentrated in vacuo. The residue is dissolved in acetone (40 ml.) and treated with lithium bromide (21 g.) at 40° for 16 hours. The mixture is concentrated in vacuo and extracted with methylene chloride (2 × 20 ml.). The methylene chloride is washed with brine (2 × 5 ml.), dried (MgSO$_4$) and concentrated in vacuo to afford 1,2-bis-(pentylthio)-3-bromopropane.

C. 1,2-Bis-(pentyloxy)-3-bromopropane

To a mixture of 3-tetrahydropyranylglycerol (0.88 g., 0.005 mole) and powdered potassium hydroxide (3 g.) in benzene (80 ml.) is added dropwise pentyl mesylate (2 g.) in benzene (20 ml.). The mixture is refluxed for 12 hours, cooled and treated with water (100 ml.) and ether (100 ml.). The organic phase is washed with brine (2 × 10 ml.) and dried (MgSO$_4$). After concentration in vacuo, the mixture is dissolved in ether (10 ml.), methanol (10 ml.) and concentrated hydrochloric acid (0.5 ml.). After stirring for 1 hour, the mixture is concentrated in vacuo, dissolved in methylene chloride (50 ml.), washed with 10% sodium bicarbonate (2 × 5 ml.), brine (2 × 5 ml.), dried (MgSO₄) and concentrated in vacuo.

To the residue dissolved in methylene chloride (5 ml.) and triethylamine (0.38 g.) at 0° to −10° is added methanesulfonyl chloride (0.32 g.). After stirring for 15 minutes, the mixture is extracted with ice water (2 × 2 ml.), cold 10% hydrochloric acid (2 × 1 ml.) and brine (2 × 1 ml.). The organic solution is dried (MgSO₄) and concentrated in vacuo.

The residue is dissolved in acetone (4 ml.) and treated with lithium bromide (1.1 g.) at 40° for 16 hours. The mixture is concentrated in vacuo and extracted with methylene chloride (2 × 5 ml.). The methylene chloride extract is washed with brine (2 × 1 ml.), dried (MgSO₄) and concentrated in vacuo to afford 1,2-bis-(pentyloxy)-3-bromopropane.

What is claimed is:
1. A compound of the formula:

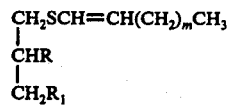

wherein R is hydroxy, halo, thiol, alkylthio, and alkoxy; R₁ is hydroxy, alkoxy, halo, thiol, and alkylthio; $m$ is an integer from 0–17.

2. The compound of claim 1, wherein R and R₁ are hydroxy, $m$ is 0–17.

3. The compound of claim 1 which compound is 3-(1-heptenylthio)-1,2-propanediol.

4. The compound of claim 1 which compound is 2-(1-heptenylthio)-1-ethanol.

* * * * *